United States Patent [19]

Louthan

[11] 4,433,134

[45] Feb. 21, 1984

[54] PREPARATION OF ALKYL MERCAPTOALKANOATES FROM UNSATURATED CARBOXYLATES AND $CO_2$-CONTAMINATED $H_2S$

[75] Inventor: Rector P. Louthan, Bartlesville, Okla.

[73] Assignee: Phillips Petroleum Company, Bartlesville, Okla.

[21] Appl. No.: 407,415

[22] Filed: Aug. 12, 1982

Related U.S. Application Data

[62] Division of Ser. No. 62,660, Aug. 1, 1979.

[51] Int. Cl.$^3$ .................... C08G 63/04; C08G 63/34
[52] U.S. Cl. .................... 528/279; 525/530; 528/293; 528/297; 528/274; 560/147; 560/154
[58] Field of Search ............. 528/279, 293, 297, 274; 525/530

[56] References Cited

U.S. PATENT DOCUMENTS

| | | | |
|---|---|---|---|
| 3,221,056 | 11/1965 | Louthan | 564/500 |
| 3,817,936 | 6/1974 | Jones | 528/293 |
| 4,052,440 | 10/1977 | Gladstone et al. | 560/154 |
| 4,067,901 | 1/1978 | Gladstone et al. | 560/154 |
| 4,113,707 | 9/1978 | Louthan et al. | 560/154 |
| 4,232,167 | 11/1980 | Louthan | 560/154 |
| 4,258,105 | 3/1981 | Williams | 528/293 X |
| 4,267,307 | 5/1981 | Louthan et al. | 528/293 |
| 4,307,225 | 12/1981 | Louthan | 528/279 |

Primary Examiner—Lucille M. Phynes

[57] ABSTRACT

The addition reaction of hydrogen sulfide with an olefinically unsaturated alkyl carboxylate, to form a product mixture at least 55 weight percent alkyl mercaptoalkanoate, is made immune from significant effects on product selectivity caused by $CO_2$ contamination of the hydrogen sulfide by selection of the addition catalyst from inorganic and organic bases having an ionization constant greater than $2.0 \times 10^{-5}$ at 25° C., such as triethylamine.

27 Claims, No Drawings

PREPARATION OF ALKYL MERCAPTOALKANOATES FROM UNSATURATED CARBOXYLATES AND $CO_2$-CONTAMINATED $H_2S$

This is a divisional of pending application Ser. No. 62,660, filed Aug. 1, 1979.

BACKGROUND OF THE INVENTION

This invention relates to the preparation of organic sulfur compounds. It further relates to a method of preparing mixed esters containing alkyl mercaptoalkanoates. It also relates to the preparation of compounds which are intermediates in the preparation of polymer sealant compositions.

The reaction of hydrogen sulfide with olefinically unsaturated organic compounds is an important process for the production of organic sulfur compounds which are intermediates in the production of compositions having a variety of commercial uses.

The reaction of $H_2S$ with an olefinically unsaturated carboxylate in the presence of a basic catalyst is a known method of preparing alkyl mercaptoalkanoates along with varying amounts of other organic sulfur compounds including thiobis(alkylalkanoates) and dithiobis(alkylalkanoates). Methods for the preparation of these "mixed esters" from $H_2S$ and an olefinically unsaturated organic compound are disclosed in U.S. Pat. Nos. 4,052,440, 4,067,901, and 4,113,707, among others.

These mercaptoalkanoates are intermediates in the preparation of polymers used to make elastomeric sealant compositions. To produce a polymer which displays the necessary physical properties after curing, it is desirable to produce a mixed ester product which is predominantly the mercaptoalkanoate. Although it is possible to remove the mercaptoalkanoate from the product mixture and then prepare the desired mixture separately, it is more economical and convenient to prepare mixed esters in the desired proportions in a single step.

A generally preferred method of preparing mixed esters for ultimate use in sealant compositions is to react $H_2S$ with a compound such as an alkyl acrylate in the presence of a weak base such as ammonium hydroxide. It has been found that during commercial production of the mixed esters, particularly during cold weather and periods of high consumption, in-plant grade $H_2S$ can absorb as much as 15 weight percent $CO_2$. The presence of this contaminant in the reaction mixture makes it impossible, even by varying the proportions of other components of the reaction mixture, to produce ester mixtures containing the alkyl mercaptoalkanoate in the desired proportions.

It is thus an object of this invention to provide a method of preparing mixed esters containing alkyl mercaptoalkanoates in the desired high proportions from unsaturated carboxylates and $CO_2$-contaminated $H_2S$.

It is a further object of the invention to minimize the reaction steps in the preparation of alkyl mercaptoalkanoates used as intermediates in the preparation of polymer sealant compositions.

SUMMARY OF THE INVENTION

In accordance with this invention, an olefinically unsaturated carboxylate is reacted with $CO_2$-containing $H_2S$ in the presence of a strongly basic catalyst to produce a mixed ester reaction product containing an alkyl mercaptoalkanoate and other organic sulfur products of the reaction including thiobis(alkylalkanoates) and dithiobis(alkylalkanoates). The reaction may be carried out in the presence of water and/or elemental sulfur co-catalysts. The $H_2S$ contains at least 1 percent $CO_2$ contamination. The use of the process of the invention makes it possible to produce a product mixture which contains predominantly the mercaptoalkanoate when the $H_2S$ reactant contains an amount of $CO_2$ contamination which would otherwise prevent the production of this compound with the desired degree of product selectivity.

DETAILED DESCRIPTION OF THE PREFERRED EMBODIMENTS

The olefinically unsaturated carboxylates suitable for use in the process of the invention are those materials represented by the formula

$$CR_2=CR+CR_2+_pCO_2R'$$

wherein R' is an alkyl radical having 1 to 5 carbon atoms; each R is selected independently from H and R'; p is zero or an integer having a value of 1, 2 or 3; and the total number of carbon atoms in all the R groups does not exceed 15 carbon atoms per molecule. Materials represented by this formula are, for example, methyl acrylate, ethyl acrylate, methyl methacrylate, ethyl 3-butenoate, n-butyl 5-hexenoate, isopropyl 5-undecenoate, n-pentyl 2-(2,2-dimethylpropyl)-5-undecenoate, t-butyl 2-methyl-2-heptenoate, methyl 3,3-dimethyl-5-hexenoate, and n-propyl 2,2,3,3,4,4,5-heptamethyl-5-heptenoate. Methyl acrylate is the presently preferred unsaturated carboxylate.

Hydrogen sulfide is generally present in an amount of 0.5 to 10 moles of $H_2S$ per mole of unsaturated carboxylate, preferably 1 to 3 moles $H_2S$ per mole of carboxylate.

Hydrogen sulfide will absorb carbon dioxide from the air, particularly when the temperature is low or during periods of high consumption when tanks of hydrogen sulfide are only partially full. The amount of $CO_2$ absorbed by the $H_2S$ under plant conditions may be as much as 15 weight percent, based on $H_2S$. However, the operability of the invention has been demonstrated with as much as 30 weight percent $CO_2$. Presently it is unlikely that sources having more than about 50 weight percent would be used. For amounts as low as 1 weight percent $CO_2$, it is desirable to use the process of the invention to obtain the desired product mix.

The basic catalysts useful in the process of the invention are bases having an ionization constant greater than $2.0 \times 10^{-5}$ at 25° C. These include strong inorganic bases such as sodium hydroxide and potassium hydroxide and strong organic bases including mono-, di- and trialkylamines. Organic amines which have the requisite properties are, for example, the following:

| Amine | Ionization Constant at 25° C.[a] |
|---|---|
| methylamine | $4.38 \times 10^{-4}$ |
| dimethylamine | $5.12 \times 10^{-4}$ |
| trimethylamine | $5.27 \times 10^{-5}$ |
| ethylamine | $5.6 \times 10^{-4}$ |
| diethylamine | $1.26 \times 10^{-3}$ |
| triethylamine | $5.65 \times 10^{-4}$ |
| dipropylamine | $8.2 \times 10^{-4}$ |
| tripropylamine | $5 \times 10^{-4}$ |
| n-butylamine | $4.1 \times 10^{-4}$ |
| iso-butylamine | $2.6 \times 10^{-4}$ |
| sec-butylamine | $3.6 \times 10^{-4}$ |

| Amine | Ionization Constant at 25° C.[a] |
|---|---|
| tert-butylamine | $2.8 \times 10^{-4}$ |
| methyldiethylamine | $2.7 \times 10^{-4}$ |
| m-methylbenzylamine | $2.4 \times 10^{-5}$ |
| 1,4-diaminobutane | $4.1 \times 10^{-4}$ |

[a]Lange's Handbook of Chemistry, 8th Edition, Handbook Publishers Inc., pages 1233-1235.

The amount of the basic catalyst used will vary depending on reaction conditions, molecular weight of the unsaturated carboxylate, and level of $CO_2$ in the hydrogen sulfide, but generally the amount of base used is from about 0.1 to 2 grams, preferably about 0.2 to 1 gram of base per mole of unsaturated carboxylate employed.

Triethylamine is the currently preferred basic catalyst for the process of the invention.

Elemental sulfur and/or water can also be used as co-catalysts for the reaction of hydrogen sulfide with an olefinically unsaturated alkyl carboxylate. As disclosed in U.S. Pat. No. 4,113,707, the reaction can be "fine tuned" to yield the desired proportion of alkyl mercaptoalkanoate and thiobis(alkylalkanoates) by adjusting the amounts of hydrogen sulfide, water and elemental sulfur present in the reaction mixture. Sulfur is generally used in the addition reaction in amounts ranging from about 0.0001 to 0.1, preferably 0.001 to 0.05, part by weight sulfur per part by weight unsaturated carboxylate. Water is generally used in amounts ranging from about 0.0001 to 0.2, preferably about 0.004 to 0.1 part by weight per part by weight unsaturated carboxylate.

The addition of hydrogen sulfide to olefinically unsaturated carboxylates can be carried out in the presence or absence of diluents. It is currently preferred to use diluents chosen from lower alcohols represented by the formula R'OH wherein R' is as described above; saturated aliphatic, saturated cycloaliphatic or aromatic hydrocarbons containing 5 to 8 carbon atoms; and cyclic or acyclic ethers containing from 4 to 8 carbon atoms. Examples of suitable diluents include methanol, ethanol, isopropanol, pentane, hexane, isooctane, cyclohexane, benzene, toluene, the xylenes, diethyl ether, di-n-butyl ether, tetrahydrofuran and p-dioxane. The alcohols are currently preferred as diluents because of their ability to influence the amount of the alkyl mercaptoalkanoate in the product mixture. Methanol is the currently preferred alcohol. When used, the diluent will generally be used in an amount within the range of 0.3 to 1 part by weight diluent per part by weight unsaturated carboxylate, but the amount of diluent is generally not critical. If an alcohol is used to influence the ester product distribution, it is used in an amount in the range of 0.02 to 4, preferably 0.04 to 0.4, parts by weight alcohol per part by weight unsaturated carboxylate.

The conditions under which the addition of hydrogen sulfide to an olefinically unsaturated carboxylate is carried out can vary depending upon the product mix desired. Temperatures in the range of 25° to 150° C. are generally suitable for the reaction; however, because of the exothermic nature of the reaction, it may be desirable to provide external cooling to the reactor. The pressure under which the reaction is generally carried out is in the range of about 200 to 2000 psig (1350 to 13,500 kPa), preferably about 200 to 500 psig (1350 to 3450 kPa). Reaction times of about 1 minute to 24 hours are generally suitable but a period of 30 minutes to 5 hours is preferable.

Following the reaction of hydrogen sulfide with the olefinically unsaturated carboxylate, it is desirable to remove the volatile diluent, unreacted starting materials and volatile by-products. This is readily accomplished by flashing the undesired volatile components of the reaction mixture. The resulting residue is a mixture containing predominantly alkyl mercaptoalkanoate and thiobis(alkylalkanoate) with small amounts (usually no more than about 1 to 5 weight percent) of higher homologs such as di- and polythiobis(alkylalkanoates). If the reaction has been carried out so that the product mixture contains the preferred product distribution of about 68 to 72 weight percent alkyl mercaptoalkanoates and 28 to 32 weight percent predominantly thiobis(alkylalkanoate), the mixture can be used directly for transesterification with a poly(oxyalkylene)-polyol to give a poly(oxyalkylene)-polyester-poly(sulfide)-polythiol for use in sealant compositions.

The alkyl mercaptoalkanoates which can be produced by the catalyzed addition reaction and used in the transesterification reaction can be represented by the formula

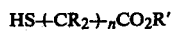
$$HS+CR_2+_nCO_2R'$$

wherein R' is an alkyl radical having 1 to 5 carbon atoms; each R is selected independently from H and R'; n is an integer having a value of from 1 to 5; and the total number of carbon atoms in the R groups does not exceed 15.

Examples of alkyl mercaptocarboxylates represented by this formula include methyl mercaptoacetate, methyl 2-mercaptopropionate, methyl 3-mercaptopropionate, ethyl 4-mercaptobutyrate, n-butyl 6-mercaptohexanoate, isopropyl 6-mercaptoundecanoate, n-pentyl 6-mercapto-2-(3-methyl-1-butyl)undecanoate, t-butyl 2-mercapto-2-methylheptanoate, methyl 3,3-dimethyl-6-mercaptohexanoate, and n-propyl 6-mercapto-2,2,3,3,4,4,5,5,6-nonamethylheptanoate.

Thiobis(alkylalkanoates) which can be produced by the process of the invention and transesterified with a poly(oxyalkylene)-polyol can be represented by the formula

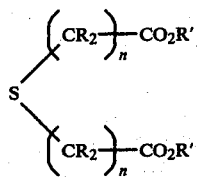

wherein R, R' and n are as defined above and the total number of carbon atoms in the R groups does not exceed 30.

Examples of thiobis(alkylalkanoates) represented by this formula include thiobis(methyl acetate), 3,3'-thiobis(methylpropionate), 4,4'-thiobis(ethyl butyrate), 6,6'-thiobis(n-butylhexanoate), and 6,6'-thiobis(isopropyl undecanoate).

Polythiobis(alkylalkanoates) of the formula

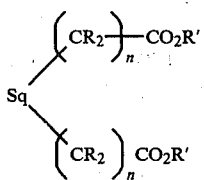

wherein R, R' and n are as defined above and q is an integer of 2 to 5, preferably 2, can also be formed in amounts up to about 1 to 5 weight percent of the total mixed esters depending upon reaction conditions.

The poly(oxyalkylene)-polyols or polyhydroxy polyethers used to make the polymer have on average more than two and generally at least 2.5, preferably at least three, pendant hydroxy groups per molecule. Such polyhydroxy polyethers or poly(oxyalkylene)-polyols have more than two, preferably three to about twelve, hydroxyl groups per molecule and molecular weights of from 200 to 20,000. These materials can be produced by the reaction of one or more epoxy-substituted hydrocarbons of the general formulas

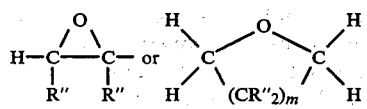

with a polyol of the general formula $Y(OH)_x$, wherein R" is selected independently from H and alkyl radicals, and the total number of carbon atoms in each molecule is no greater than about 20; wherein m is an integer from 1 to about 10, preferably 1 to 3; and wherein Y can be a hydrocarbon moiety having at least 2 and usually 3 to 40 carbon atoms per moiety and a valence equal to x, x being an integer of at least 2 and usually 3 to about 20, and the number of carbon atoms per molecule of $Y(OH)_x$ is equal to or greater than x.

Polyols that are used in the preparation of the poly(oxyalkylene)-polyols or polyhydroxy polyethers comprise hydroxy-substituted hydrocarbons, preferably saturated aliphatics, saturated cycloaliphatics, aryls, or combinations of these which are substituted with an average of more than two and preferably at least three hydroxyl groups per molecule. In the presently preferred embodiment of this invention, the polyols $Y(OH)_x$ can have from 2 to about 12 hydroxyl groups per molecule and can contain from 3 to about 20 carbon atoms per molecule. Examples of polyols which can be represented by the formula $Y(OH)_x$ are ethylene glycol, 1,3-propanediol, 2-butene-1,4-diol, 1,4-cyclohexanediol, 2-ethylhexane-1,3-diol, glycerine, pentaerythritol, erythritol, 1,3,8-trihydroxycyclododecane, estriol, 1,4,5,8-naphthalenetetrol, di(p-hydroxyphenyl) phenyl methanol, 1,2,6-hexanetriol, and 1,2,4,6,7,9,12,14,15,17,19,20-eicosanedodecol.

The poly(oxyalkylene)-polyols or polyhydroxy polyethers of the invention can be prepared by contacting at least one polyol of the formula $Y(OH)_x$, as defined above, with an epoxy-substituted hydrocarbon, as defined above, under suitable polymerization conditions known in the art. For example, glycerine can be contacted with an excess of propylene oxide (1,2-epoxypropane) under elevated pressure and in the presence of suitable polymerization promoters. Products of this type, such as Niax Polyol LHT-67 (a trademark), can be obtained from commercial sources. In the preparation of poly(oxyalkylene)-polyols having on average more than 2 pendant hydroxyl groups per molecule, mixtures of the above polyols such as at least one diol and another polyol can be reacted with the epoxy-substituted hydrocarbons defined above to form poly(oxyalkylene)-polyols having more than two pendant hydroxy groups on average per molecule. For example, a mixture of 1,4-butanediol and 1,2,6-hexanetriol can be reacted with ethylene oxide to produce a poly(oxyethylene)-polyol having an average of more than 2 pendant hydroxy groups per molecule. Alternatively, a poly(oxyalkylene)-polyol produced, for example, by the reaction of a diol such as ethylene glycol with an alkylene oxide such as propylene oxide, can be mixed with another poly(oxyalkylene)-polyol produced, for example, by the reaction of a triol such as 1,2,6-hexanetriol with an alkylene oxide such as propylene oxide. As another alternative, up to about 30 weight percent of the poly(oxyalkylene)-polyol can be replaced with a polyol having recurring ester linkages, e.g., an average of about 2 to about 5 ester linkages per molecule, in place of at least a portion of the ether linkages, produced, e.g., by reaction of a lactone such as caprolactone with a polyol such as ethylene glycol or with an alkylene oxide-polyol condensation product such as diethylene glycol.

Examples of the epoxy-substituted hydrocarbons of the above formulas that can be employed with the polyols to form the poly(oxyalkylene)-polyol include 1,2-epoxypropane, 1,2-epoxyethane, 1,2-epoxydocosane, 10,11 epoxydocosane, 2,3-epoxy-4,5-dimethyldodecane, 1,3-epoxypropane, 1,12-epoxydodecane, 1,12-epoxy-2,11-dibutyldodecane, and 1,4-epoxy-2-(2,2-dimethyltetradecyl)-butane.

Transesterification catalysts useful in the invention for the transesterification of the mixture of alkyl mercaptoalkanoate and thiobis(alkylalkanoate) with poly(oxyalkylene)-polyols include those of the formula $M(OR''')_4$, wherein $R'''$ is an alkyl group having from 1 to 10 carbon atoms and M is titanium or zirconium. It is presently preferred to use tetraalkyl titanates in which M is titanium and each $R'''$ group contains 3 to 8 carbon atoms.

Mixtures of alkyl mercaptoalkanoates and thiobis(alkylalkanoates), and other thio compounds as defined above, if any, useful in this invention can contain 50 to 95 weight percent alkyl mercaptoalkanoate, preferably 55 to 80 weight percent alkyl mercaptoalkanoate, most preferably for reasons of convenience and economy, 68 to 72 weight percent alkyl mercaptoalkanoate.

To improve the efficiency of the transesterification reaction it is often desirable to exclude materials, such as water, which are detrimental to the reaction. Water can be excluded by, for example, purging the poly(oxyalkylene)-polyol at elevated temperature with a dry, inert gas.

It is convenient to run the transesterification reaction in the absence of diluent, but inert diluents can be used. Suitable diluents include saturated aliphatic, saturated cycloaliphatic or aromatic hydrocarbons containing from 5 to 8 carbon atoms such as pentane, hexane, isooctane, cyclohexane, benzene, toluene and the xylenes, as well as acyclic or cyclic ethers containing 4 to 8 carbon atoms such as diethyl ether, di-n-butyl ether, tetrahydrofuran and p-dioxane.

In the transesterification step it is convenient to use the mixed esters and poly-(oxyalkylene)-polyol in amounts ranging from 0.8 to 1.2 equivalents of ester group in the mixed esters per equivalent of hydroxy group in the poly(oxyalkylene)-polyol, preferably 1.0 to 1.1, and more preferably 1.04 to 1.07, equivalents of ester per equivalent of hydroxy. The transesterification catalyst is generally used in an amount ranging from 0.1 to 4 and preferably 0.2 to 2 grams of catalyst per gram equivalent of hydroxy groups in the poly(oxyalkylene)-polyol.

The transesterification reaction to produce the poly(oxyalkylene)-polyester-poly(monosulfide)-polythiol and poly(oxyalkylene)-polyester-poly(monosulfide)-poly(disulfide)-polythiol is normally carried out at a temperature in the range of 125° to 235° C., preferably from 165° to 225° C., for a time period in the range of 0.5 to 72 hours, preferably from 6 to 30 hours. The pressure under which the transesterification reaction occurs can be whatever is convenient, from subatmospheric to superatmospheric, depending on temperature and volatility of reaction components. For example, reaction pressures can range from 0.1 to 100 atmospheres, but those from 1 atmosphere to 10 atmospheres are preferred.

Conditions of temperature and pressure are chosen to provide for the continuous removal overhead of R'OH during the course of the transesterification. One skilled in the art will recognize that the continuous removal of a lower alcohol from a transesterification reaction system provides the driving force for the transesterification to occur to a high degree. If, however, one desires a lower degree of transesterification, e.g., the equilibrium value, then removal of the alcohol overhead will not be necessary.

At the completion of the transesterification reaction, as evidenced by the cessation of evolution of R'OH, the poly(oxyalkylene)-polyester-poly(monosulfide)-polythiol or poly(oxyalkylene)-polyester-poly(monosulfide)-poly(disulfide)-polythiol will generally require no further treatment or working prior to use if no diluent has been used. If, however, further purification or treatment of the product is desired, then well-known procedures such as washing or solvent extraction may be employed to provide product with the desired degree of purity.

The poly(oxyalkylene)-polyester-poly(monosulfide)-polythiol and poly(oxyalkylene)-polyester-poly(monosulfide)-poly(disulfide)-polythiol prepared can be used immediately after preparation or can be stored for a period of time prior to use. They are useful in a variety of sealant and coating formulations such as those described fully in U.S. Pat. Nos. 3,803,089, 3,817,936, 3,829,526, 3,843,381, 3,857,876, 3,919,077 and 3,931,078, the disclosures of which are hereby incorporated by reference.

The poly(oxyalkylene)-polyester-poly(monosulfide)-polythiol or poly(oxyalkylene)-polyester-poly(monosulfide)-poly(disulfide)-polythiol produced from the mixed esters of this invention is readily oxidatively coupled or cured in an appropriate formulation to form a cured or coupled composition which is useful as a sealant. The sealant comprises the poly(oxyalkylene)-polyester-poly(monosulfide)-polythiol or poly(oxyalkylene)-polyester-poly(monosulfide)-poly(disulfide)-polythiol, a filler and a curing agent. The filler generally comprises an inert inorganic filler and a pigment, either inorganic or organic. Other materials such as cure modifiers, plasticizers, extenders, stabilizers, modifiers, adhesion promoters, and the like may be present. Generally, the sealant will contain 10 to 99, preferably 30 to 75 percent by weight of the poly(oxyalkylene)-polyester-poly(monosulfide)-polythiol or poly(oxyalkylene)-polyester-poly(monosulfide)-poly(disulfide)-polythiol and the remainder nonelastomer ingredients as set out above.

The poly(oxyalkylene)-polyester-poly(monosulfide)-polythiols or poly(oxyalkylene)-polyester-poly(monosulfide)-poly(disulfide)-polythiols can be cured in a sealant formulation with conventional curing agents including free oxygen-containing fluids such as, for example, air; organic peroxide and hydroperoxides such as, for example, di-tert-butyl peroxide and cumene hydroperoxide; metal oxides such as, for example, the oxides of lead, zinc, manganese, calcium, barium, copper, mercury, tin and iron; metal salts of carboxylic acids such as, for example, lead stearate, zinc laurate, zinc acetate; ammonium persulfate; sulfur; and the like. The curing time will vary with the polymer, the curing agent, the sealant formulation, and the temperature. In general, sufficient curing agent is employed to convert at least about 7 percent of the pendant thiol groups to polysulfide groups.

The following examples show the effects on product selectivity of carbon dioxide contamination of hydrogen sulfide and how those effects can be overcome by the use of the catalysts of the invention.

EXAMPLE I

Control Run with No $CO_2$ Contamination

This is a control run performed under preferred conditions for obtaining the desired product ratio when $CO_2$ contamination of the $H_2S$ reactant is not present. The catalyst used was ammonium hydroxide.

Three hundred milliliters of methanol, 12 grams elemental sulfur, 21.6 grams concentrated ammonium hydroxide, and 816 grams (23.9 moles) hydrogen sulfide were charged into a one-gallon stainless steel autoclave equipped with a stirrer, thermowell, pressure gauge, and an internal cooling coil. With no heating or cooling, 1376 grams (16 moles) methyl acrylate was metered into the stirred reactor over a period of about 45 minutes. The temperature increased from about 26° C. initially to about 56° C. at the end of the charging period, while the reaction pressure decreased from 277 psig to 200 psig over the same period. The reaction mixture was stirred an additional one hour to ensure that the reaction was complete. The excess hydrogen sulfide was vented and the remaining solution discharged and analyzed by GLC. The mixture was analyzed by GLC using a 2 ft. by ¼ in. column packed with silicone rubber and programmed between 100° C. to 300° C. at 25° C./minute using a helium gas flow of 60 milliliters per minute. There was obtained a 100% conversion of methyl acrylate to yield a mixture of 71.5 weight percent methyl 3-mercaptopropionate and 28.5 weight percent of what was believed to be essentially 3,3'-thiobis(methylpropionate), although no determination of the amount of di- and polythiobis(methylpropionate) was made for the products of the examples. The desired product mixture for ultimate use in cured polymeric sealants is about 68 to 72 weight percent methyl 3-mercaptopropionate and the balance essentially all 3,3'-thiobis(methylpropionate).

EXAMPLE II

Control Run Showing Effect of $CO_2$ Contamination

This is a control run illustrating the effect carbon dioxide as an impurity in hydrogen sulfide has on product selectivity. The run described in Example I was repeated except that 20.4 grams (2.5 weight percent, based on $H_2S$) of $CO_2$ was added with the $H_2S$ reactant to simulate impure $H_2S$. GLC analysis of the reaction product indicated a 100% conversion of methyl acrylate with a product mixture of 67.3 weight percent methyl 3-mercaptopropionate and 32.7 weight percent 3,3'-thiobis(methylpropionate). Table I lists the product selectivity when varying amounts of $CO_2$ are present.

The data show that the presence of $CO_2$ has the effect of reducing the proportion of methyl 3-mercaptopropionate present in the reaction mixture.

TABLE I

Effect on Product Selectivity of
$CO_2$-Contaminated $H_2S$ Using $NH_4OH$ as Catalyst

| Mole Ratio of $H_2S$/Methyl Acrylate | Wt. % $CO_2$ Based on $H_2S$ Charged | Wt. % by GLC | |
|---|---|---|---|
| | | Methyl 3-Mercapto-propionate | 3,3'-Thiobis-(methyl-propionate)[a] |
| 1.5/1 | 0 | 71.5 | 28.5 |
| 1.5/1 | 2.5 | 67.3 | 32.7 |
| 1.5/1 | 5.0 | 67.8 | 32.2 |
| 1.5/1 | 10.0 | 62.2 | 37.8 |
| 1.5/1 | 15.0 | 59.9 | 40.1 |
| 1.5/1 | 30.0 | 56.3 | 43.7 |

[a] A small amount (about 1 to 5 weight percent, based on the total weight of the mixed esters) of 3,3'-thiobis(methylpropionate) is present as well as higher polysulfides but all are considered as negligible.

EXAMPLE III

Control Run Showing Effect of Additional $H_2S$ When $CO_2$ Contamination Present This is a control run illustrating the effect on product distribution of adding more $H_2S$ to attempt to overcome the effects of the $CO_2$ present. It is known that adjusting the amount of $H_2S$ can affect the proportion of methyl 3-mercaptopropionate formed. The run described in Example I was repeated using various ratios of $H_2S$/methyl acrylate and various $CO_2$ levels. The results given in Table II show that the deleterious effect of $CO_2$ contamination can be to some extent counteracted by increasing the amount of $H_2S$, but that the depressing effect on methyl 3-mercaptopropionate formation is not completely overcome.

TABLE II

Effect on Product Selectivity of
$CO_2$-Contaminated $H_2S$ Using $NH_4OH$ as Catalyst
Plus Various Amounts of $H_2S$

| Mole Ratio of $H_2S$/Methyl Acrylate | Wt. % $CO_2$ Based on $H_2S$ Charged | Wt. % by GLC | |
|---|---|---|---|
| | | Methyl 3-Mercapto-propionate | 3,3'-Thiobis-(methyl-propionate) |
| 1.5/1 | 10 | 62.2 | 37.8 |
| 1.5/1 | 15 | 59.9 | 40.1 |
| 1.5/1 | 30 | 56.3 | 43.7 |
| 2.0/1 | 0 | 72.3 | 27.7 |
| 2.0/1 | 10 | 61.8 | 38.2 |
| 2.0/1 | 15 | 63.5 | 36.5 |
| 2.0/1 | 30 | 64.2 | 35.8 |
| 2.5/1 | 0 | 76.1 | 23.9 |
| 2.5/1 | 10 | 74.8 | 25.2 |
| 2.5/1 | 30 | 67.8 | 32.2 |
| 4.0/1 | 0 | 78.2 | 21.8 |
| 4.0/1 | 15 | 53.9 | 46.1 |

EXAMPLE IV

Invention Run Using Triethylamine as Catalyst

This is an invention run illustrating that $CO_2$ dissolved in $H_2S$ has no significant effect on product distribution when triethylamine is used as the catalyst. The procedure described in Example II was repeated with triethylamine (6 grams in 15 ml $H_2O$) substituted for concentrated ammonium hydroxide as the catalyst. The results listed in Table III show that $CO_2$ contamination has no significant effect on product distribution when triethylamine is the catalyst.

TABLE III

Effect on Product Selectivity of
$CO_2$-Contaminated $H_2S$ Using Triethylamine as Catalyst

| Mole Ratio of $H_2S$/Methyl Acrylate | Wt. % $CO_2$ Based on $H_2S$ Charged | Wt. % by GLC | |
|---|---|---|---|
| | | Methyl 3-Mercapto-propionate | 3,3'-Thiobis-(methyl-propionate) |
| 1.5/1 | 0 | 68.1 | 31.9 |
| 1.5/1 | 15 | 71.9 | 28.1 |
| 1.5/1 | 30 | 67.1 | 32.9 |
| 2.0/1 | 0 | 79.7 | 20.3 |
| 2.0/1 | 15 | 76.8 | 23.2 |
| 2.0/1 | 30 | 78.6 | 21.4 |
| 2.5/1 | 0 | 82.2 | 17.8 |
| 2.5/1 | 15 | 80.9 | 19.1 |
| 2.5/1 | 30 | 81.3 | 18.7 |
| 4.0/1 | 0 | 76.5 | 23.5 |
| 4.0/1 | 15 | 81.6 | 18.4 |

Table IV offers a comparison of the data obtained in the control runs with the data of the invention runs. The data show that when ammonium hydroxide is used as the basic addition catalyst in the addition of hydrogen sulfide to methyl acrylate to produce a product mix of about 70/30 weight percent methyl 3-mercaptopropionate/3,3'-thiobis(methylpropionate), the reaction is sensitive to the presence of $CO_2$ in the hydrogen sulfide so that significantly less methyl 3-mercaptopropionate and more 3,3'-thiobis(methylpropionate) are produced.

The data also show that, while increasing the $H_2S$ concentration counteracts part of the effect of $CO_2$ contamination on product distribution, its effectiveness is greatly dependent upon the amount of $CO_2$ present. By contrast, use of triethylamine as the catalyst overcomes the $CO_2$ effect on product distribution in a relatively consistent fashion so that the amount of methyl 3-mercaptopropionate remains in or near the desired 68 to 72 weight percent rage.

The use of stronger bases such as triethylamine to overcome the effects of $CO_2$ contamination thus represents a way to economically and conveniently prepare intermediates for polymer sealant compositions in the desired product proportions when the $H_2S$ reactant is contaminated with $CO_2$.

TABLE IV

Comparison of Product Selectivity of CO$_2$-Contaminated H$_2$S Using NH$_4$OH and Triethylamine as Catalyst

| Mole Ratio of H$_2$S/Methyl Acrylate | Wt. % CO$_2$ Based on H$_2$S Charged | Wt. % Methyl 3-Mercaptopropionate by GLC[a] | |
|---|---|---|---|
| | | NH$_4$OH Catalyzed | (C$_2$H$_5$)$_3$N Catalyzed |
| 1.5/1 | 0 | 71.5 | 68.1 |
| 1.5/1 | 10 | 62.2 | — |
| 1.5/1 | 15 | 59.9 | 71.9 |
| 1.5/1 | 30 | 56.3 | 67.1 |
| 2.0/1 | 0 | 72.3 | 79.7 |
| 2.0/1 | 10 | 61.8 | — |
| 2.0/1 | 15 | 63.5 | 76.8 |
| 2.0/1 | 30 | 64.2 | 78.6 |
| 2.5/1 | 0 | 76.1 | 82.2 |
| 2.5/1 | 10 | 74.8 | — |
| 2.5/1 | 15 | 66.5 | 80.9 |
| 2.5/1 | 30 | 67.8 | 81.3 |
| 4.0/1 | 0 | 78.2 | 76.5 |
| 4.0/1 | 15 | 53.9 | 81.6 |

[a]Balance is considered to be predominately 3,3'-thiobis(methylpropionate).

EXAMPLE V

Invention Run Using Diethylamine

This is an invention run illustrating that CO$_2$ dissolved in H$_2$S has no significant effect on product distribution when diethylamine is used as the basic catalyst. The procedure of Example I was followed substituting 6 grams of diethylamine for ammonium hydroxide. The mole ratio of H$_2$S to methyl acrylate was 1.5:1.0. There was obtained a 100% conversion of methyl acrylate to yield a mixture of 68.9 weight percent methyl 3-mercaptopropionate and 31.1 weight percent of predominately 3,3'-thiobis(methylpropionate).

This run was repeated with 122.4 grams (15 weight percent) CO$_2$ added to the H$_2$S. A 100% conversion of methyl acrylate was obtained with a product yield of 71.3 weight percent methyl 3-mercaptopropionate and 28.7 weight percent of predominately 3,3'-thiobis(methylpropionate).

TABLE V

Product Distribution Using Diethylamine Catalyst

| Mole Ratio of H$_2$S/Methyl Acrylate | Wt. % CO$_2$ Based on H$_2$S Charged | Wt. % Methyl 3-Mercaptopropionate[a] | |
|---|---|---|---|
| | | NH$_4$OH Catalyzed | (C$_2$H$_5$)$_3$NH Catalyzed |
| 1.5/1 | 0 | 71.5 | 68.9 |
| 1.5/1 | 15 | 59.9 | 71.3 |

[a]Balance is considered to be predominately 3,3'-thiobis(methylpropionate)

I claim:
1. A method comprising:
reacting carbon dioxide-containing hydrogen sulfide with an olefinically unsaturated carboxylate of the formula

$$CR_2=CR-(CR_2)_p-CO_2R'$$

wherein R' is an alkyl radical containing from 1 to 5 carbon atoms; each R is selected independently from hydrogen and R'; p is selected from 0, 1, 2 and 3; and the total number of carbon atoms in all the R groups does not exceed 15,
in the presence of a basic catalyst having an ionization constant of at least 2.0×10$^{-5}$ at 25° C., to form a reaction product comprising mixed esters, and
reacting thus-obtained mixed esters in the presence of a transesterification catalyst with a poly(oxyalkylene)-polyol produced by reacting one or more epoxy-substituted hydrocarbons of the formula

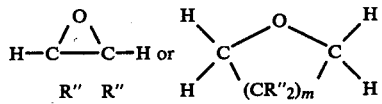

wherein each R" is selected independently from H and alkyl, the total number of carbon atoms in the molecule represented by the formula does not exceed 20, and m is an integer of from 1 to 10, with a polyol of the formula $$Y(OH)_x$$

wherein Y is a hydrocarbon moiety having at least two carbon atoms and a valence equal to the value of x, and x is an integer of at least two.

2. The method of claim 1 in which the hydrogen sulfide contains at least 1 weight percent carbon dioxide based on the weight of hydrogen sulfide.

3. The method of claim 1 in which the basic catalyst is selected from alkylamines.

4. The method of claim 3 in which the basic catalyst is a tertiary alkylamine.

5. The method of claim 3 in which the basic catalyst is selected from methylamine, dimethylamine, trimethylamine, ethylamine, diethylamine, triethylamine, dipropylamine, tripropylamine, n-butylamine, iso-butylamine, sec-butylamine, tert-butylamine, methyldiethylamine, m-methylbenzylamine, and 1,4-diaminobutane.

6. The method of claim 3 in which the basic catalyst is selected from dialkylamines and trialkylamines.

7. The method of claim 2 in which the basic catalyst is diethylamine.

8. The method of claim 2 in which the catalyst is triethylamine.

9. The method of claim 2 in which the basic catalyst is an alkali metal hydroxide.

10. The method of claim 1 in which the basic catalyst is present in an amount of from 0.1 to 2 grams of catalyst per mole of the olefinically unsaturated carboxylate.

11. The method of claim 2 in which the reaction is carried out in the presence of sulfur.

12. The method of claim 2 or claim 11 in which the reaction is carried out in the presence of water.

13. The method of claim 2 or claim 11 in which the reaction is carried out in the presence of a lower aliphatic alcohol.

14. The method of claim 12 in which the reaction is carried out in the presence of a lower aliphatic alcohol.

15. The method of claim 14 in which the lower aliphatic alcohol is present in an amount of about 0.02 to 4 parts by weight, the water is present in an amount of about 0.0001 to 0.2 parts by weight, and the sulfur, when present, is present in an amount of about 0.0001 to 0.2 parts by weight, all based on one part by weight of the olefinically unsaturated carboxylate.

16. The method of claim 1 or claim 2 in which the alkyl mercaptoalkanoate is present in the mixed ester reaction product in an amount of at least 55 weight percent based on the weight of the mixed esters.

17. The method of claim 1 or claim 2 in which the alkyl mercaptoalkanoate is present in the mixed ester reaction product in an amount of from about 68 weight percent to about 72 weight percent.

18. The method of claim 17 in which the hydrogen sulfide is present in an amount of from 1 to 3 moles per mole of the olefinically unsaturated carboxylate, the sulfur, when present, is present in an amount of from 0.002 to 0.4 parts by weight per part by weight of the olefinically unsaturated carboxylate, and the basic catalyst is present in an amount of from about 0.2 to 1 gram per mole of the olefinically unsaturated carboxylate.

19. The method of claim 17 in which the olefinically unsaturated carboxylate is methyl acrylate, the basic catalyst is an alkylamine, and methanol is present in an amount of from 0.04 to 0.4 parts by weight per part by weight unsaturated carboxylate.

20. The method of claim 19 in which the carbon dioxide is present in an amount of at least 2.5 weight percent based on the weight of the hydrogen sulfide.

21. The method of claim 20 in which the transesterification reaction product is a poly(oxyalkylene)-polyester-poly(monosulfide)-poly(disulfide)-polythiol.

22. The method of claim 20 in which the transesterification reaction product is a poly(oxyalkylene)-polyester-poly(monosulfide)-polythiol.

23. The method of claim 20 in which the alkylamine is selected from diethylamine and triethylamine.

24. The method of claim 20 in which the mixed ester reaction product comprises methyl mercaptopropionate and 3,3'-thiobis(methylpropionate).

25. The method of claim 1 in which the transesterification catalyst is $M(OR''')_4$, wherein $R'''$ is an alkyl group having from 1 to 10 carbon atoms and M is titanium or zirconium.

26. A method comprising adding a filler to a composition prepared according to the method of claim 1.

27. A method comprising curing a composition prepared according to the method of claim 1.

* * * * *